(12) United States Patent
Furusato et al.

(10) Patent No.: US 11,623,904 B2
(45) Date of Patent: Apr. 11, 2023

(54) METHOD FOR PRODUCING CYCLOBUTANEDIOL COMPOUND

(71) Applicant: JNC CORPORATION, Tokyo (JP)

(72) Inventors: Shinichi Furusato, Chiba (JP); Toshiyuki Kawanabe, Chiba (JP); Kaori Tsuruoka, Kumamoto (JP); Hironao Sajiki, Gifu (JP); Tsuyoshi Yamada, Gifu (JP); Kwihwan Park, Gifu (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 17/204,848

(22) Filed: Mar. 17, 2021

(65) Prior Publication Data

US 2021/0300847 A1 Sep. 30, 2021

(30) Foreign Application Priority Data

Mar. 26, 2020 (JP) .............................. JP2020-055655

(51) Int. Cl.
*C07C 29/145* (2006.01)
*C07C 29/56* (2006.01)
*B01J 23/46* (2006.01)

(52) U.S. Cl.
CPC .......... *C07C 29/145* (2013.01); *B01J 23/462* (2013.01); *C07C 29/56* (2013.01); *C07C 2601/04* (2017.05)

(58) Field of Classification Search
CPC ... C07C 29/145; C07C 29/56; C07C 2601/04; B01J 23/462
See application file for complete search history.

(56) References Cited

U.S. PATENT DOCUMENTS

| 2,936,324 A | * | 5/1960 | Hasek | .................. C07C 35/045 |
| | | | | 568/839 |
| 3,000,906 A | * | 9/1961 | Hasek | ..................... C07C 45/72 |
| | | | | 549/263 |
| 5,258,556 A | * | 11/1993 | Sumner, Jr. | ............. C07C 45/89 |
| | | | | 568/301 |

FOREIGN PATENT DOCUMENTS

| WO | 2012078384 | 6/2012 |
| WO | 2012078439 | 6/2012 |
| WO | 2016094478 | 6/2016 |
| WO | 2016094479 | 6/2016 |

OTHER PUBLICATIONS

Yasunari Monguchi et al., "Palladium on carbon-catalyzed solvent-free and solid-phase hydrogenation and Suzuki-Miyaura reaction", Tetrahedron, Sep. 2011, pp. 8628-8634.

* cited by examiner

*Primary Examiner* — Rosalynd A Keys
(74) *Attorney, Agent, or Firm* — JCIPRNET

(57) ABSTRACT

Provided is a process in which a cyclobutanediol compound having a high cis:trans ratio can be stably obtained. The cyclobutanediol compound having a cis:trans ratio of 1.5:1 to 5000:1 is produced by using at least one compound selected from a group consisting of a cyclobutanedione compound, a cyclobutane ketol compound, and a cyclobutanediol compound as a raw material, and performing a catalytic hydrogenation reaction and an isomerization reaction in the cyclobutanediol compound in a solid phase state in the presence of a metal catalyst without adding a solvent.

5 Claims, No Drawings

METHOD FOR PRODUCING CYCLOBUTANEDIOL COMPOUND

CROSS-REFERENCE TO RELATED APPLICATIONS

This application claims the priority benefit of Japanese Patent Application No. 2020-055655, filed on Mar. 26, 2020. The entirety of the above-mentioned patent application is hereby incorporated by reference herein and made a part of this specification.

BACKGROUND

Technical Field

The disclosure relates to a method for producing a cyclobutanediol compound.

Related Art

Cyclobutanediol compounds represented by 2,2,4,4-tetramethylcyclobutane-1,3-diol (hereinafter, TMCBD) are used in the production of various polymer materials. For example, polyesters derived from dicarboxylic acids and TMCBD have high glass transition temperature and excellent weather resistance and hydrolysis stability when compared with similar polyesters made from other commonly used polyester-forming diols.

Stereoisomers of the hydroxyl group of TMCBD include cis isomers and trans isomers, and are often obtained in a range that the cis:trans ratio of TMCBD which is obtained by catalytic hydrogenation of 2,2,4,4-tetramethylcyclobutane-1,3-dione (hereinafter, TMCBK) is about 1:1 to about 1.5:1. It is known that the cis:trans ratio affects important properties of polyester having TMCBD, and stable control of the cis:trans ratio is important because it leads to stability in quality of polyester.

As a method for adjusting the cis:trans ratio of TMCBD, there is a reported case of only isomerization without the production of net TMCBD. A raw material having a cis:trans ratio of 0:1 to 1.5:1 in a liquid phase is isomerized to a resultant having a different cis:trans ratio. However, this method is isomerization in a state of being completely dissolved in a solvent, and therefore the cis:trans ratio can be increased only to about 1.5:1 at the most (Patent literature 1).

In addition, there is a reported case in which hydrogenation is performed at a reaction temperature higher than the dew point of TMCBD in the gas phase in catalytic hydrogenation from TMCBK to TMCBD. However, in this method, the cis:trans ratio of the TMCBD obtained is about 1:1 to about 1.6:1, which is not greatly different from that of the completely dissolved system, and the efficiency is low in a producing process, for example, 100 to 500 mol of hydrogen is required (Patent literature 2).

Furthermore, as a method for increasing the cis:trans ratio of TMCBD, there is a reported case using reaction crystallization in which a cis isomer is precipitated during the reaction. In this method, water, hydrocarbons, or a mixture thereof is used as a solvent, TMCBK is brought into contact with hydrogen in the presence of a ruthenium catalyst to thereby precipitate the produced cis-TMCBD and obtain TMCBD having a high cis:trans ratio in the reaction system. However, as an example, filtration is performed with cis-TMCBD precipitated, and the filtrate is washed away with a solvent which dissolves cis-TMCBD to obtain cis-TMCBD. As a result, the amount of solvent used in the steps from the reaction to the collection of cis-TMCBD increases, and it cannot be said that the process is environmentally friendly from the viewpoint of green chemistry (Patent literatures 3 to 4).

On the other hand, from the viewpoint of green sustainable chemistry, there are reported cases of hydrogenation in a solid phase state in which no solvent is used and the raw material, intermediate, resultant and catalyst are solid, and reported cases of Suzuki coupling. As for hydrogenation, it has been confirmed that in the presence of a palladium catalyst, a good hydrogenation reaction can be carried out using unsaturated hydrocarbons, azide derivatives, benzyl ethers, and the like under a condition that the partial pressure of hydrogen is atmospheric pressure (Non-Patent literature 1).

A method of reducing a cyclobutanedione compound such as TMCBK using a ruthenium catalyst in a solid phase state without using a solvent has not been studied so far. From the viewpoint of green chemistry, it is necessary to develop a process for producing a cyclobutanediol compound such as TMCBD that is harmonious with environment, and there is a need to develop a process in which a cyclobutanediol compound having a high cis:trans ratio can be stably obtained.

LITERATURE OF RELATED ART

Patent Literature

Patent literature 1: International Publication No. 2012/078439
Patent literature 2: International Publication No. 2012/078384
Patent literature 3: International Publication No. 2016/094478
Patent literature 4: International Publication No. 2016/094479

Non-Patent Literature

Non-Patent literature 1: Tetrahedron 67 (2011) 8628-8634

SUMMARY

The disclosure is to develop a process for producing a cyclobutanediol compound that is harmonious with environment from the viewpoint of green chemistry and capable of stably obtaining a cyclobutanediol compound having a high cis:trans ratio.

The present inventors have found that a cyclobutanediol compound having a high cis:trans ratio can be stably obtained by performing a catalytic hydrogenation reaction from a cyclobutanedione compound to a cyclobutanediol compound or cis-trans isomerization of a cyclobutanediol compound in a solid phase state in the presence of a metal catalyst without using a solvent.

The disclosure has been completed based on the above findings.

That is, the disclosure is as follows.

[1] A method for producing a cyclobutanediol compound having a cis:trans ratio of 1.5:1 to 5000:1, the cyclobutanediol compound being produced by using at least one compound selected from a group consisting of a cyclobutanedione compound, a cyclobutane ketol compound, and a cyclobutanediol compound as a raw material, and performing a catalytic hydrogenation reaction and an isomerization reaction in the cyclobutanediol compound in a solid phase state in the presence of a metal catalyst without adding a solvent.

[2] The method for producing a cyclobutanediol compound according to item [1], wherein the cyclobutanedione compound is a cyclobutanedione compound represented by general formula (1),

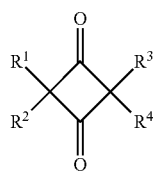

(1)

wherein, $R^1$, $R^2$, $R^3$ and $R^4$ are independently hydrogen, alkyl having 1 to 20 carbon atoms, halogenated alkyl having 1 to 20 carbon atoms, cycloalkyl having 3 to 20 carbon atoms, or aryl having 4 to 30 carbon atoms, and $R^1$, $R^2$, $R^3$ and $R^4$ may be bonded to each other to form a cyclic structure.

[3] The method for producing a cyclobutanediol compound according to item [1] or [2], wherein the metal catalyst is a catalyst containing at least one metal selected from Ru, Pt, Pd, Rh, Ni, and Cu.

[4] The method for producing a cyclobutanediol compound according to any one of items [1] to [3], wherein the metal catalyst is a catalyst containing Ru.

[5] The method for producing a cyclobutanediol compound according to any one of items [1] to [4], wherein the carrier of the metal catalyst is activated carbon, carbon, alumina, silica, ceramic, or cellulose.

[6] The method for producing a cyclobutanediol compound according to any one of items [1] to [5], wherein the partial pressure of hydrogen in the reaction is in a range of 0.02 to 50 MPa and the reaction temperature is in a range of 10 to 150° C.

DESCRIPTION OF THE EMBODIMENTS

An embodiment according to the disclosure is described. Moreover, the disclosure is not limited to the following embodiment.

A method for producing a cyclobutanediol compound of the disclosure is characterized in that by performing a catalytic hydrogenation reaction and an isomerization reaction in a cyclobutanediol compound in a solid phase state without adding a solvent to a raw material and a metal catalyst, the cis:trans ratio of the cyclobutanediol compound becomes higher than the cis:trans ratio of a cyclobutanediol compound which is obtained by performing the reactions in a solution system using a conventional method.

At least one compound selected from a group consisting of a cyclobutanedione compound, a cyclobutane ketol compound, and a cyclobutanediol compound can be used as the raw material without particular limitation.

For example, the cyclobutanedione compound is a cyclobutanedione compound represented by general formula (1),

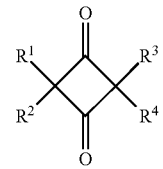

(1)

wherein, $R^1$, $R^2$, $R^3$ and $R^4$ are independently hydrogen, alkyl having 1 to 20 carbon atoms, halogenated alkyl having 1 to 20 carbon atoms, cycloalkyl having 3 to 20 carbon atoms, or aryl having 4 to 30 carbon atoms, and $R^1$, $R^2$, $R^3$ and $R^4$ may be bonded to each other to form a cyclic structure.

The metal of the metal catalyst is at least one metal selected from Ru, Pt, Pd, Rh, Ni, and Cu. Ru is preferable.

The carrier of the metal catalyst is at least one carrier selected from activated carbon, carbon, graphite, graphene, graphene oxide, alumina, silica, titania, ceramics, cellulose and hydroxyapatite. Carbon and alumina are preferable.

The amount of the metal carried by the metal catalyst is 0.1 wt % to 15 wt %, preferably 0.2 wt % to 10 wt %.

The metal catalyst may be in a dry state or in a state of being wetted with water or the like. The amount of water in the wetted state is 1 wt % to 200 wt %, preferably 5 wt % to 100 wt %.

Although the catalyst concentration may be varied within a wide range, it is adjusted to a range of 0.001 mol % to 50 mol % (mole quantity of the catalyst metal with respect to mole quantity of the raw material), preferably 0.01 mol % to 20 mol %, and more preferably 0.1 mol % to 10 mol %.

The embodiment of the disclosure is carried out under a predetermined reaction temperature and mixing condition by charging the raw material and the metal catalyst into a reactor, introducing hydrogen by substituting the inside of the rector in a solid phase state without adding a solvent.

The reactor may be a container which is capable of performing gas substitution, and a flask, an autoclave, or the like can be used. In addition, a rotary evaporator that allows the container to rotate to mix the materials inside, or a method of feeding hydrogen to a column-type fixed bed in which the raw material and the catalyst are mixed and filled in advance can also be used. Furthermore, a fluidized bed reactor that can treat solids semi-continuously, a Nauta mixer, a ribbon blender, a "SV mixer" and a "PV mixer" manufactured by Kobelco Eco-Solutions Co., Ltd. can also be used.

The raw material and the metal catalyst may be charged individually or may be charged in a premixed state. In order to suppress the sudden load of the stirring power of the reactor, the raw material and the metal catalyst may be charged under the operation of the stirring of the reactor.

The methods for hydrogen substitution in the reactor include a method of introducing a large amount of hydrogen to substitute the inside of the reactor, a method of repeating pressurization and purging using hydrogen or an inert gas, a method of repeating the introduction of hydrogen after the inside of the reactor is depressurized, and the like. The embodiment of the disclosure is in a solid phase state without the addition of a solvent, and thus there is no concern about evaporation of the solvent. Therefore, the method of repeating the introduction of hydrogen after the inside of the reactor is depressurized is preferable.

The hydrogen in the reactor may be mixed with inert gas, and the partial pressure of hydrogen is in a range of 0.02 MPa to 50 MPa, preferably 0.05 MPa to 5 MPa, and more preferably 0.08 MPa to 0.98 MPa.

The reaction temperature is in a range of 10° C. to 150° C., preferably 30° C. to 100° C., and more preferably 50° C. to 80° C.

As for the mixing condition, it is sufficient that the sufficiently mixed state of the raw material and the metal catalyst are maintained. When the raw material and the metal catalyst are charged in the premixed state, it is not necessary to specially mix in the reactor.

After the reaction, the catalyst can be easily removed from the reaction mixture by dissolving the reaction mixture in a solvent to make it non-uniform and filtering the reaction mixture. The catalyst may be repeatedly used for the catalytic hydrogenation reaction and the isomerization reaction without further treatment, or may be repeatedly used in a state of being wetted with water or the like used first.

The reaction mixture can be dissolved in at least one solvent selected from water, alcohols, ethers, hydrocarbons, ketones and esters. The solvent includes, for example, water, methanol, ethanol, 1-propanol, 2-propanol, 1-butanol, 2-butanol, 2-ethylhexanol, diethyl ether, diisopropyl ether, tetrahydrofuran, hexane, heptane, cyclohexane, acetone, methyl ethyl ketone, cyclohexanone, ethyl acetate, n-propyl acetate, n-butyl acetate, isobutyl acetate, isobutyl isobutyrate, and a mixture thereof. Water, methanol, 2-propanol, acetone, and ethyl acetate are preferable in terms of availability and operability.

EXAMPLE

Hereinafter, the disclosure is described in more detail with reference to examples. However, the disclosure is not limited thereto.

Example 1

(Example of Hydrogenation Under Atmospheric Pressure)

"Personal organic synthesizer ChemiStation™ PPM-5512 type" manufactured by Tokyo Rikakikai Co., Ltd. is used as the reactor.

7.14 mmol of TMCBK being the raw material and 1.5 g of 5 wt % Ru/C (manufactured by Fuji Film Wako Pure Chemical Industries, Ltd.) being the catalyst (ruthenium content in catalyst Ru/C is 1/10 mol of the raw material) are charged into a test tube of 120 mL. After degassing the inside of the test tube, a hydrogen gas balloon is attached and the inside is substituted under a hydrogen gas atmosphere, and then the reaction temperature is set to 60° C., and the reaction is carried out by stirring at a stirring speed of 300 rpm for 6 hours.

(Post-Treatment after Reaction)

Then, 40 mL of ethyl acetate is added to the obtained reactant to dissolve the raw material, the resultant and the like, and filtration is performed using a membrane filter (manufactured by ADVANTEC, DISMIC (registered trademark), 13HP020AN, pore diameter 0.20 μm) to thereby obtain a reaction filtrate from which the catalyst Ru/C has been removed. In addition, the catalyst Ru/C used in the reaction is separately cleaned by 10 mL of ethyl acetate, and the cleaning liquid is recovered. The ratio of the raw material to the reaction product is calculated by mixing the cleaning liquid with the previously obtained reaction filtrate and measuring by a gas chromatograph (manufactured by Shimadzu Corporation). Moreover, the post-reactants include TMCBK being the raw material, TMCBO being a monoreduced form, cis-TMCBD being a cis isomer of a direduced form, trans-TMCBD being a trans isomer of a direduced form, and others being by-products in which the cyclobutane skeleton is opened. The gas chromatography (GC) composition is shown in the table below. In addition, the ratio of cis isomer to trans isomer of TMCBD is also shown in the table.

Examples 2 to 3

The same operations are carried out except that the reaction temperature of Example 1 is changed to 70° C. and 80° C., respectively.

Examples 4 to 6

The same operations are carried out as in Example 1 except that the catalyst of Example 1 is changed to 5 wt % Ru/Al$_2$O$_3$ (manufactured by Fuji Film Wako Pure Chemical Industries, Ltd.) and the reaction temperature is changed to 60° C., 70° C., and 80° C., respectively.

The results of Examples 1 to 6 are collectively shown in Table 1 below.

TABLE 1

| | Catalyst | Reaction Temperature [° C.] | GC composition [GC %] | | | | | TMCBD cis:trans ratio |
| --- | --- | --- | --- | --- | --- | --- | --- | --- |
| | | | TMCBK | TMCBO | cis-TMCBD | trans-TMCBD | Others | |
| Example 1 | Ru/C | 60 | 0.0 | 0.6 | 77.7 | 18.2 | 3.6 | 4.3:1 |
| Example 2 | | 70 | 0.2 | 0.6 | 78.8 | 16.8 | 3.7 | 4.7:1 |
| Example 3 | | 80 | 0.4 | 0.8 | 73.8 | 17.4 | 7.7 | 4.2:1 |
| Example 4 | Ru/Al$_2$O$_3$ | 60 | 0.2 | 2.3 | 77.4 | 18.1 | 2.0 | 4.3:1 |
| Example 5 | | 70 | 2.1 | 4.0 | 88.3 | 3.0 | 2.7 | 29.4:1 |
| Example 6 | | 80 | 0.0 | 3.8 | 80.7 | 7.1 | 8.4 | 11.4:1 |

The results of Examples 1 to 6 show that TMCBD can be quantitatively obtained from TMCBK by performing the catalytic hydrogenation reaction in a solid phase state without adding a solvent, and the cis ratio in TMCBD is as high as about 4 to about 30.

Example 7

(Example of Hydrogenation Under Pressurization)

"Personal organic synthesizer ChemiStation™ PPV-4460 type" manufactured by Tokyo Rikakikai Co., Ltd. is used as the reactor.

1.96 mmol of TMCBK being the raw material and 0.13 g of 5 wt % Ru/C containing 50 wt % of water (A-type/manufactured by N.E. Chemcat) being the catalyst (ruthenium content in catalyst Ru/C is 1/60 mol of the raw material) are charged into a reaction tube of 42 mL. Then, after connecting a gas line and substituting under a hydrogen gas atmosphere, the partial pressure of hydrogen is set to 0.8 MPa, the reaction temperature is set to 50° C., and the reaction is carried out by stirring at a stirring speed of 600 rpm for 4 hours.

The post-treatment after the reaction is carried out in the same manner as in Example 1.

Examples 8 to 10

The same operations are carried out except that the reaction temperature of Example 7 is changed to 60° C., 70° C., and 80° C., respectively.

Comparative Example 1

(Example of Hydrogenation Under Pressurization in Methanol)

"Personal organic synthesizer ChemiStation™ PPV-4460 type" manufactured by Tokyo Rikakikai Co., Ltd. is used as the reactor.

7.82 mmol of TMCBK being the raw material, 0.53 g of 5 wt % Ru/C containing 50 wt % of water (A-type/manufactured by N.E. Chemcat) being the catalyst (ruthenium content in catalyst Ru/C is 1/60 mol of the raw material), and 40 mL of methanol being the reaction solvent are charged into a reaction tube of 190 mL. Then, after connecting the gas line and substituting under the hydrogen gas atmosphere, the partial pressure of hydrogen is set to 0.8 MPa, the reaction temperature is set to 80° C., and the reaction is carried out by stirring at a stirring speed of 600 rpm for 4 hours.

Then, the obtained reaction solution is filtered using a membrane filter (manufactured by ADVANTEC, DISMIC (registered trademark), 13HP020AN, pore diameter 0.20 μm) to obtain a reaction filtrate from which the catalyst Ru/C has been removed. Subsequent operations are carried out in the same manner as in Example 1.

Comparative Examples 2 to 3

The same operations are carried out except that the reaction solvent of Comparative example 1 is changed to isopropyl alcohol and ethyl acetate, respectively.

The results of Examples 7 to 10 and Comparative examples 1 to 3 are collectively shown in Table 2 below.

TABLE 2

| | Solvent | Reaction temperature [° C.] | GC composition [GC %] | | | | | TMCBD cis:trans ratio |
| --- | --- | --- | --- | --- | --- | --- | --- | --- |
| | | | TMCBK | TMCBO | cis-TMCBD | trans-TMCBD | Others | |
| Example 7 | None | 50 | 0.1 | 1.0 | 61.7 | 37.0 | 0.3 | 1.7:1 |
| Example 8 | None | 60 | 0.0 | 0.8 | 78.1 | 20.9 | 0.2 | 3.7:1 |
| Example 9 | None | 70 | 0.2 | 1.4 | 70.0 | 27.8 | 0.6 | 2.5:1 |
| Example 10 | None | 80 | 0.0 | 2.0 | 73.2 | 24.0 | 0.8 | 3.1:1 |
| Comparative example 1 | MeOH | 80 | 0.0 | 0.1 | 42.2 | 57.6 | 0.0 | 0.7:1 |
| Comparative example 2 | iPrOH | 80 | 0.0 | 0.1 | 59.8 | 39.9 | 0.2 | 1.5:1 |
| Comparative example 3 | AcOEt | 80 | 0.0 | 0.1 | 50.8 | 48.7 | 0.4 | 1.0:1 |

The comparison between Examples 7 to 10 and Comparative examples 1 to 3 shows that the cis ratio in TMCBD is increased by performing the catalytic hydrogenation reaction in a solid phase state without adding a solvent.

Example 11

(Example of Isomerization Under Pressurization by Ru/C)

"Personal organic synthesizer ChemiStation™ PPV-4460 type" manufactured by Tokyo Rikakikai Co., Ltd. is used as the reactor.

1.96 mmol of TMCBD before isomerization and 0.13 g of 5 wt % Ru/C containing 50 wt % of water (A-type/manufactured by N.E. Chemcat) being the catalyst (ruthenium content in catalyst Ru/C is 1/60 mol of TMCBD before isomerization) are charged into a reaction tube of 42 mL. Then, after connecting the gas line and substituting under the hydrogen gas atmosphere, the partial pressure of hydrogen is set to 0.8 MPa, the reaction temperature is set to 60° C., and the reaction is carried out by stirring at a stirring speed of 600 rpm for 5.6 hours.

The post-treatment after the reaction is carried out in the same manner as in Example 1.

Example 12

(Example of Isomerization Under Pressurization by Ru/Al$_2$O$_3$)

The same operations are carried out except that the catalyst of Example 10 is changed to 5 wt % Ru/Al$_2$O$_3$ (manufactured by Fuji Film Wako Pure Chemical Industries, Ltd.).

The TMCBD composition before isomerization and the results of Examples 11 to 12 are shown in Table 3 below.

TABLE 3

| | | GC composition [GC %] | | | | | TMCBD |
|---|---|---|---|---|---|---|---|
| | Catalyst | TMCBK | TMCBO | cis-TMCBD | trans-TMCBD | Others | cis:trans ratio |
| Before isomerization | | 0.0 | 0.1 | 60.7 | 37.4 | 1.7 | 1.6:1 |
| Example 11 | Ru/C containing 50 wt % of water | 0.0 | 0.0 | 67.3 | 31.3 | 1.3 | 2.2:1 |
| Example 12 | Ru/Al$_2$O$_3$ | 0.0 | 0.08 | 77.5 | 21.0 | 1.4 | 3.7:1 |

The results of Examples 10 and 11 show that the cis ratio of TMCBD is increased by performing the isomerization reaction in the cyclobutanediol compound in a solid phase state without adding a solvent.

Example 13

(Example of Hydrogenation of Dispiro [5.1.5.1] Tetradecane-7,14-Dione (Hereinafter, Referred to as DSTDK) by Ru/C)

"Personal organic synthesizer ChemiStation™ PPM-5512 type" manufactured by Tokyo Rikakikai Co., Ltd. is used as the reactor.

7.13 mmol of DSTDK being the raw material and 1.50 g of 5 wt % Ru/C (manufactured by Fuji Film Wako Pure Chemical Industries, Ltd.) being the catalyst (ruthenium content in catalyst Ru/C is 1/10 mol of the raw material) are charged into a reaction tube of 120 mL. After degassing the inside of the reaction tube, the hydrogen gas balloon is attached and the inside is substituted under the hydrogen gas atmosphere, then the reaction temperature is set to 70° C., and the reaction is carried out by stirring at a stirring speed of 300 rpm for 6 hours.

Then, 40 mL of ethyl acetate is added to the obtained reactant to dissolve the raw material, the resultant, and the like, and filtration is performed using a membrane filter (manufactured by ADVANTEC, DISMIC (registered trademark), 13HP020AN, pore diameter 0.20 μm) to thereby obtain a reaction filtrate from which the catalyst Ru/C has been removed. In addition, the catalyst Ru/C used in the reaction is separately cleaned by 10 mL of ethyl acetate, and the cleaning liquid is recovered. The ratio of the raw material to the reactant is calculated by mixing the cleaning liquid with the previously obtained reaction filtrate and measuring by a gas chromatograph (manufactured by Shimadzu Corporation). Moreover, the post-reactants include DSTDK being the raw material, DSTDO being a monoreduced form, cis-DSTDD being a cis isomer of a direduced form, trans-DSTDD being a trans isomer of a direduced form, and others being by-products in which the cyclobutane skeleton is opened. The GC composition is shown in the table below.

Example 14

(Example of Hydrogenation Under Pressurization by Ru/Al$_2$O$_3$)

The same operations are carried out except that the catalyst of Example 13 is changed to 5 wt % Ru/Al$_2$O$_3$ (manufactured by Fuji Film Wako Pure Chemical Industries, Ltd.).

The results of Examples 13 to 14 are shown in Table 4 below.

TABLE 4

| | | GC composition [GC %] | | | | | DSTDD |
|---|---|---|---|---|---|---|---|
| | Catalyst | DSTDK | DSTDO | cis-DSTDD | trans-DSTDD | Others | cis:trans ratio |
| Example 13 | Ru/C containing 50 wt % of water | 0.0 | 13.9 | 85.5 | 0.55 | 0.0 | 155.5:1 |
| Example 14 | Ru/Al$_2$O$_3$ | 2.6 | 70.3 | 23.7 | 3.4 | 0.0 | 7.0:1 |

The results of Examples 13 and 14 show that DSTDD can be quantitatively obtained from DSTDK by performing the catalytic hydrogenation reaction in a solid phase state without adding a solvent, and the cis ratio in DSTDD is as high as about 7 to about 155.

According to the method for producing a cyclobutanediol compound according to the disclosure, a cyclobutanediol compound having a higher cis isomer ratio than before can be obtained under mild reaction conditions, and the producing process is environmentally friendly in terms of green chemistry because no reaction solvent is used.

INDUSTRIAL APPLICABILITY

The cyclobutanediol compound having a high cis:trans ratio obtained by the method for producing a cyclobutanediol compound of the disclosure can be used as a raw material for polyester having high stability and stable quality in terms of glass transition temperature, impact strength, weather resistance, and hydrolysis stability.

What is claimed is:
1. A method for producing a cyclobutanediol compound, comprising:
   using at least one compound selected from a group consisting of a cyclobutanedione compound, a cyclobutane ketol compound, and a cyclobutanediol compound as a raw material; and performing a catalytic hydrogenation reaction and an isomerization reaction in the cyclobutanediol compound in a solid phase state in the presence of a metal catalyst without adding a solvent to produce the cyclobutanediol compound having a cis:trans ratio of 1.7:1 to 155.5:1, wherein the metal catalyst is a catalyst containing Ru, a partial pressure of hydrogen in both of the catalytic hydrogenation reaction and the isomerization reaction is in a range of 0.1 to 0.98 MPa, and a reaction temperature is in a range of 40° C. to 90° C.

2. The method for producing a cyclobutanediol compound according to claim 1, wherein the cyclobutanedione compound is a cyclobutanedione compound represented by general formula (1),

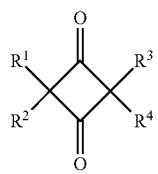

(1)

wherein, $R^1$, $R^2$, $R^3$ and $R^4$ are independently hydrogen, alkyl having 1 to 20 carbon atoms, halogenated alkyl having 1 to 20 carbon atoms, cycloalkyl having 3 to 20 carbon atoms, or aryl having 4 to 30 carbon atoms, and $R^1$, $R^2$, $R^3$ and $R^4$ may be bonded to each other to form a cyclic structure.

3. The method for producing a cyclobutanediol compound according to claim 1, wherein a carrier of the metal catalyst is activated carbon, carbon, alumina, silica, ceramic, or cellulose.

4. A method for producing a cyclobutanediol compound, comprising:
using at least one compound selected from a group consisting of a cyclobutane ketol compound and a cyclobutanediol compound as a raw material; and
performing a catalytic hydrogenation reaction and an isomerization reaction in the cyclobutanediol compound in a solid phase state in the presence of a metal catalyst without adding a solvent to produce the cyclobutanediol compound having a cis:trans ratio of 1.7:1 to 155.5:1, wherein the metal catalyst is a catalyst containing Ru, a partial pressure of hydrogen in both of the catalytic hydrogenation reaction and the isomerization reaction is in a range of 0.1 to 0.98 MPa, and a reaction temperature is in a range of 40° C. to 90° C.

5. The method for producing a cyclobutanediol compound according to claim 4, wherein a carrier of the metal catalyst is activated carbon, carbon, alumina, silica, ceramic, or cellulose.

* * * * *